(12) United States Patent
Sherwood et al.

(10) Patent No.: US 8,873,220 B2
(45) Date of Patent: Oct. 28, 2014

(54) SYSTEMS AND METHODS TO CONNECT SINTERED ALUMINUM ELECTRODES OF AN ENERGY STORAGE DEVICE

(75) Inventors: Gregory J. Sherwood, Shoreview, MN (US); Michael J. Root, Lino Lakes, MN (US); Jay E. Daley, Coon Rapids, MN (US); Eric Stemen, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 229 days.

(21) Appl. No.: 12/968,571

(22) Filed: Dec. 15, 2010

(65) Prior Publication Data

US 2011/0149474 A1   Jun. 23, 2011

Related U.S. Application Data

(60) Provisional application No. 61/288,095, filed on Dec. 18, 2009.

(51) Int. Cl.
| | | |
|---|---|---|
| *H01G 9/00* | (2006.01) | |
| *H01G 5/38* | (2006.01) | |
| *H01G 9/008* | (2006.01) | |
| *H01G 9/012* | (2006.01) | |
| *H01G 9/14* | (2006.01) | |
| *H01G 9/08* | (2006.01) | |
| *A61N 1/375* | (2006.01) | |
| *A61N 1/378* | (2006.01) | |

(52) U.S. Cl.
CPC ............... *H01G 9/012* (2013.01); *H01G 9/008* (2013.01); *A61N 1/375* (2013.01); *H01G 9/14* (2013.01); *A61N 1/3782* (2013.01); *H01G 9/08* (2013.01)
USPC ............ 361/503; 361/502; 361/522; 361/541

(58) Field of Classification Search
USPC ...................... 361/503, 522, 541, 306.1, 328
See application file for complete search history.

(56) References Cited

U.S. PATENT DOCUMENTS

| | | |
|---|---|---|
| 3,025,441 A | 3/1962 | West |
| 3,331,759 A | 7/1967 | Middelhoek et al. |
| 3,445,731 A | 5/1969 | Saeki et al. |

(Continued)

FOREIGN PATENT DOCUMENTS

| | | |
|---|---|---|
| EP | 0877400 A1 | 11/1998 |
| EP | 1470267 B1 | 4/2009 |

(Continued)

OTHER PUBLICATIONS

Bocek, Joseph M, et al., "Method and Apparatus for Charging Partitioned Capacitors", U.S. Appl. No. 11/462,301, filed Aug. 3, 2006, 53 pgs.

(Continued)

*Primary Examiner* — Jayprakash N Gandhi
*Assistant Examiner* — Dion R Ferguson
(74) *Attorney, Agent, or Firm* — Schwegman, Lundberg & Woessner, P.A.

(57) ABSTRACT

This document provides an apparatus including a sintered electrode, a second electrode and a separator material arranged in a capacitive stack. A conductive interconnect couples the sintered electrode and the second electrode. Embodiments include a clip interconnect. In some embodiments, the interconnect includes a comb-shaped connector. In some embodiments, the interconnect includes a wire snaked between adjacent sintered substrates.

11 Claims, 10 Drawing Sheets

(56) References Cited

U.S. PATENT DOCUMENTS

| | | | |
|---|---|---|---|
| 3,627,520 A | 12/1971 | Rogers | |
| 3,638,083 A | 1/1972 | Dornfeld et al. | |
| 3,647,415 A | 3/1972 | Yano et al. | |
| 4,059,116 A | 11/1977 | Adams | |
| 4,085,397 A | 4/1978 | Yagher | |
| 4,107,762 A | 8/1978 | Shirn et al. | |
| 4,406,286 A | 9/1983 | Stein | |
| 4,720,767 A | 1/1988 | Chan et al. | |
| 4,840,122 A | 6/1989 | Nerheim | |
| 4,882,115 A | 11/1989 | Schmickl | |
| 5,062,025 A | 10/1991 | Verhoeven et al. | |
| 5,115,378 A * | 5/1992 | Tsuchiya et al. | 361/502 |
| RE34,879 E | 3/1995 | Bocchi et al. | |
| 5,468,254 A | 11/1995 | Hahn et al. | |
| 5,591,211 A | 1/1997 | Meltzer | |
| 5,591,217 A | 1/1997 | Barreras | |
| 5,634,938 A | 6/1997 | Swanson et al. | |
| 5,660,737 A * | 8/1997 | Elias et al. | 216/6 |
| 5,763,911 A | 6/1998 | Matthews et al. | |
| 5,807,397 A | 9/1998 | Barreras | |
| 5,930,109 A | 7/1999 | Fishler | |
| 6,115,235 A | 9/2000 | Naito | |
| 6,141,205 A | 10/2000 | Nutzman et al. | |
| 6,161,040 A | 12/2000 | Blunsden | |
| 6,193,779 B1 | 2/2001 | Reichert et al. | |
| 6,241,751 B1 | 6/2001 | Morgan et al. | |
| 6,310,757 B1 | 10/2001 | Tuzuki et al. | |
| 6,347,032 B2 | 2/2002 | Naito | |
| 6,350,406 B1 | 2/2002 | Satou et al. | |
| 6,351,371 B1 | 2/2002 | Yoshida et al. | |
| 6,385,031 B1 | 5/2002 | Lerche et al. | |
| 6,456,877 B1 | 9/2002 | Fishler | |
| 6,459,566 B1 | 10/2002 | Casby et al. | |
| 6,493,212 B1 | 12/2002 | Clarke et al. | |
| 6,509,588 B1 | 1/2003 | O'Phelan et al. | |
| 6,560,089 B2 | 5/2003 | Miltich et al. | |
| 6,678,559 B1 | 1/2004 | Breyen et al. | |
| 6,687,118 B1 | 2/2004 | O'Phelan et al. | |
| 6,699,265 B1 | 3/2004 | O'Phelan et al. | |
| 6,775,127 B2 | 8/2004 | Yoshida | |
| 6,778,860 B2 | 8/2004 | Ostroff et al. | |
| 6,785,123 B2 | 8/2004 | Keser | |
| 6,801,424 B1 | 10/2004 | Nielsen et al. | |
| 6,807,048 B1 | 10/2004 | Nielsen et al. | |
| 6,850,405 B1 | 2/2005 | Mileham et al. | |
| 6,855,234 B2 | 2/2005 | D'Astolfo, Jr. | |
| 6,865,417 B2 | 3/2005 | Rissmann et al. | |
| 6,914,769 B2 | 7/2005 | Welsch et al. | |
| 6,952,608 B2 | 10/2005 | Ostroff | |
| 6,954,670 B2 | 10/2005 | Ostroff | |
| 7,024,246 B2 | 4/2006 | Acosta et al. | |
| 7,327,557 B2 | 2/2008 | Poplett | |
| 7,522,957 B2 | 4/2009 | Ostroff | |
| 7,531,010 B1 | 5/2009 | Feger et al. | |
| 7,564,677 B2 * | 7/2009 | Poplett | 361/508 |
| 7,760,488 B2 | 7/2010 | Breznova et al. | |
| 8,179,663 B2 | 5/2012 | Brabeck et al. | |
| 2003/0169560 A1 | 9/2003 | Welsch et al. | |
| 2004/0147960 A1 | 7/2004 | O'Phelan et al. | |
| 2004/0147961 A1 | 7/2004 | O'Phelan et al. | |
| 2004/0240155 A1 | 12/2004 | Miltich et al. | |
| 2005/0017888 A1 | 1/2005 | Sherwood et al. | |
| 2006/0035152 A1 | 2/2006 | Nishimura et al. | |
| 2006/0139580 A1 | 6/2006 | Conner | |
| 2006/0139850 A1 | 6/2006 | Rorvick et al. | |
| 2006/0166088 A1 | 7/2006 | Hokanson et al. | |
| 2006/0174463 A1 | 8/2006 | O'Phelan et al. | |
| 2006/0249774 A1 * | 11/2006 | Sherwood | 257/303 |
| 2007/0109723 A1 | 5/2007 | Kuriyama et al. | |
| 2007/0188980 A1 | 8/2007 | Hossick-Schott | |
| 2008/0030927 A1 | 2/2008 | Sherwood | |
| 2008/0198534 A1 | 8/2008 | Lee et al. | |
| 2008/0208270 A1 | 8/2008 | Linder et al. | |
| 2009/0231782 A1 | 9/2009 | Fujita et al. | |
| 2009/0237862 A1 | 9/2009 | Nielsen et al. | |
| 2009/0242415 A1 | 10/2009 | Yoshimitsu | |
| 2009/0273884 A1 | 11/2009 | Shimizu et al. | |
| 2010/0010562 A1 | 1/2010 | Daley et al. | |
| 2010/0110614 A1 | 5/2010 | Umemoto et al. | |
| 2010/0110615 A1 | 5/2010 | Nishimura et al. | |
| 2010/0157510 A1 | 6/2010 | Miyachi et al. | |
| 2010/0193731 A1 | 8/2010 | Lee et al. | |
| 2010/0195261 A1 | 8/2010 | Sweeney et al. | |
| 2010/0226066 A1 | 9/2010 | Sweeney et al. | |
| 2010/0226070 A1 | 9/2010 | Yang et al. | |
| 2011/0038098 A1 | 2/2011 | Taira et al. | |
| 2011/0149475 A1 | 6/2011 | Sherwood et al. | |
| 2011/0152958 A1 | 6/2011 | Sherwood et al. | |
| 2011/0152959 A1 | 6/2011 | Sherwood | |
| 2011/0152960 A1 | 6/2011 | Daley et al. | |
| 2011/0152961 A1 | 6/2011 | Sherwood | |
| 2013/0141842 A1 | 6/2013 | Sherwood et al. | |

FOREIGN PATENT DOCUMENTS

| | | |
|---|---|---|
| JP | 2003522420 A | 7/2013 |
| WO | WO-2006139850 A1 | 6/2006 |
| WO | WO-2011075506 A2 | 6/2011 |
| WO | WO-2011075506 A3 | 6/2011 |
| WO | WO-2011075508 A2 | 6/2011 |
| WO | WO-2011075508 A3 | 6/2011 |
| WO | WO-2011075511 A2 | 6/2011 |
| WO | WO-2011075511 A3 | 6/2011 |

OTHER PUBLICATIONS

"U.S. Appl. No. 12/968,555, Notice of Allowance mailed Apr. 2, 2013", 9 pgs.

"U.S. Appl. No. 12/968,555, Notice of Allowance mailed Nov. 23, 2012", 9 pgs.

"U.S. Appl. No. 12/968,555, Response filed Oct. 29, 2012 to Restriction Requirement mailed Sep. 27, 2012", 7 pgs.

"U.S. Appl. No. 12/968,555, Restriction Requirement mailed Sep. 27, 2012", 7 pgs.

"U.S. Appl. No. 12/968,555, Supplemental Notice of Allowability mailed Dec. 26, 2012", 2 pgs.

"U.S. Appl. No. 12/968,584, Non Final Office Action mailed Jan. 30, 2013", 11 pgs.

"International Application Serial No. PCT/US2010/060432, Corrected International Preliminary Report on Patentability mailed May 11, 2012", 22 pgs.

"International Application Serial No. PCT/US2010/060432, International Preliminary Report on Patentability mailed Apr. 27, 2012", 16 pgs.

"International Application Serial No. PCT/US2010/060432, Invitation to Pay Additional Fees mailed Sep. 13, 2011", 9 pgs.

"International Application Serial No. PCT/US2010/060432, Search Report mailed Dec. 5, 2011", 6 pgs.

"International Application Serial No. PCT/US2010/060432, Written Opinion mailed Dec. 5, 2011", 14 pgs.

"International Application Serial No. PCT/US2010/060437, International Preliminary Report on Patentability", 7 pgs.

"International Application Serial No. PCT/US2010/060437, Search Report mailed Sep. 13, 2011", 4 pgs.

"International Application Serial No. PCT/US2010/060437, Written Opinion mailed Sep. 13, 2011", 6 pgs.

"International Application Serial No. PCT/US2010/060444, International Preliminary Report on Patentability mailed Jun. 28, 2012", 8 pgs.

"International Application Serial No. PCT/US2010/060444, International Search Report mailed Sep. 14, 2011", 4 pgs.

"International Application Serial No. PCT/US2011/060444, Written Opinion mailed Sep. 14, 2011", 7 pgs.

"U.S. Appl. No. 12/968,523, Non Final Office Action mailed Jun. 21, 2013", 12 pgs.

"U.S. Appl. No. 12/968,536, Non Final Office Action mailed Jun. 21, 2013", 7 pgs.

"U.S. Appl. No. 12/968,561, Response filed Jul. 31, 2013 to Restriction Requirement mailed Jun. 21, 2013", 7 pgs.

(56) References Cited

OTHER PUBLICATIONS

"U.S. Appl. No. 12/968,561, Restriction Requirement mailed Jun. 21, 2013", 6 pgs.

"U.S. Appl. No. 12/968,584, Non Final Office Action mailed Jul. 31, 2013", 12 pgs.

"U.S. Appl. No. 12/968,584, Response filed Apr. 26, 2013 to Non Final Office Action mailed Jan. 30, 2013", 10 pgs.

US 8,503,164, 8/2013, Sherwood et al. (withdrawn).

"U.S. Appl. No. 12/968,523, Response filed Sep. 23, 2013 to Non Final Office Action mailed Jun. 21, 2013", 8 pgs.

"U.S. Appl. No. 12/968,523, Non Final Office Action mailed Oct. 15, 2013", 9 pgs.

"U.S. Appl. No. 12/968,536, Response filed Sep. 23, 2013 to Non Final Office Action mailed Jun. 21, 2013", 7 pgs.

"U.S. Appl. No. 12/968,536, Non Final Office Action mailed Oct. 2, 2013", 17 pgs.

"U.S. Appl. No. 12/968,555, Notice of Allowance mailed Aug. 28, 2013", 8 pgs.

"U.S. Appl. No. 12/968,561, Notice of Allowance mailed Nov. 13, 2013", 11 pgs.

"U.S. Appl. No. 12/968,561, Response filed Sep. 30, 2013 to Restriction Requirement mailed Aug. 29, 2013", 7 pgs.

"U.S. Appl. No. 12/968,561, Restriction Requirement mailed Aug. 29, 2013", 7 pgs.

"U.S. Appl. No. 12/968,584, Response filed Oct. 29, 2013 to Non Final Office Action mailed Jul. 31, 2013", 10 pgs.

"Japanese Application Serial No. 2012-544737, Office Action mailed Nov. 5, 2013", With English Translation, 6 pgs.

* cited by examiner

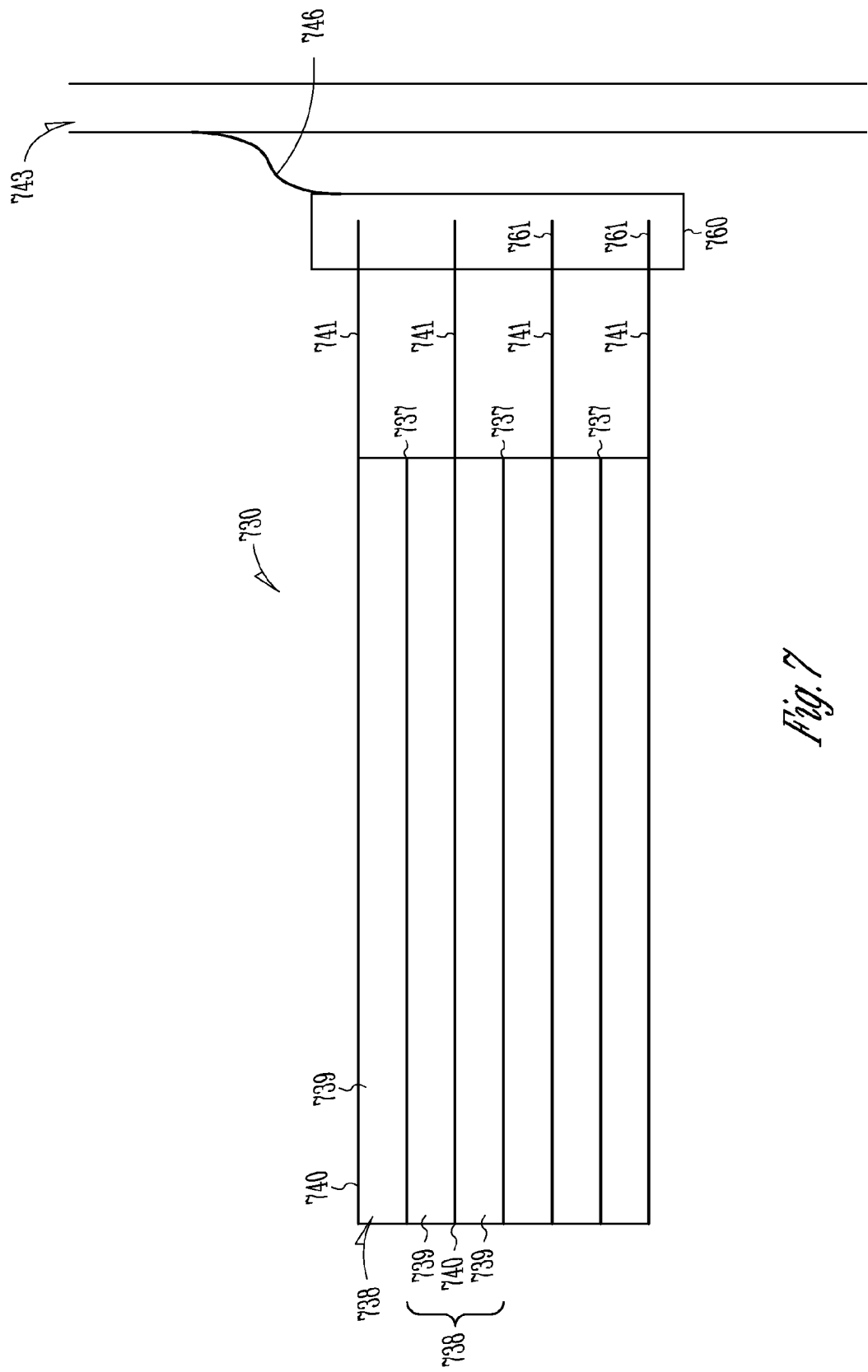

SYSTEMS AND METHODS TO CONNECT SINTERED ALUMINUM ELECTRODES OF AN ENERGY STORAGE DEVICE

CROSS-REFERENCE TO RELATED APPLICATIONS

This application claims the benefit of U.S. Provisional Application No. 61/288,095, filed on Dec. 18, 2009, under 35 U.S.C. §119(e), which is incorporated herein by reference in its entirety.

TECHNICAL FIELD

This document relates generally to energy storage and particularly to sintered electrodes to store energy in an implantable medical device.

BACKGROUND

Electrical stimulation therapy has been found to benefit some patients. For example, some patients suffer from an irregular heartbeat or arrhythmia and may benefit from application of electrical stimulation to the heart. Some patients suffer from a particular type of arrhythmia called a fibrillation. Fibrillations may affect different regions of the heart, such as the atria or the ventricles. When a fibrillation occurs in the ventricles, the heart's ability to pump blood is dramatically reduced, putting the patient at risk of harm. It has been found that applying an electrical stimulation to the patient can effectively treat patients suffering disorders such as from fibrillation by restoring a regular heartbeat.

Because disorders such as fibrillations can happen at any time, it is helpful to have a device that is easily accessible to treat them. In some cases, it is helpful if that device is portable or implantable. In developing a device that is portable or implantable, it is helpful to have access to subcomponents that are compact and lightweight and that can perform to desired specifications.

SUMMARY

This disclosure relates to apparatus for coupling sintered electrodes of an energy storage device. An apparatus according to one embodiment includes an electrode including a sintered material deposited on a conductive substrate, the conductive substrate having a substrate flexibility greater than a material flexibility of the material, the substrate including a substrate connection portion, a separator disposed in a capacitor stack with the electrode in alignment, a second electrode disposed in the capacitor stack in alignment, the second electrode including a connection portion, and a conductive interconnect physically and electrically coupling the substrate connection portion and the connection portion of the second electrode, the substrate connection portion and the connection portion of the second electrode adapted to deform to accommodate displacement of the electrode with respect to the second electrode. An embodiment includes a slotted interconnect. Additional embodiments include a interconnect comprising a wire snaked between two sintered substrates.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof. The scope of the present invention is defined by the appended claims and their legal equivalents.

BRIEF DESCRIPTION OF THE DRAWINGS

The drawings illustrate generally, by way of example, various embodiments discussed in the present document. The drawings are for illustrative purposes only and may not be to scale.

FIG. 7 shows a capacitor element according to an embodiment of the present subject matter.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than an embodiment. The following detailed description is, therefore, not to be taken in a limiting sense, and the scope is defined only by the appended claims, along with the full scope of legal equivalents to which such claims are entitled.

Energy storage capacitors are used with implantable devices to provide stimulation energy. Advances continue to take place to increase the energy storage of such capacitors while also reducing the size of the capacitors. As these advances take place they present new challenges for efficiently and economically producing the more advanced energy storage capacitors. The present disclosure relates to energy storage devices that include flexible foil substrates and interconnects to couple multiple substrates together. The flexible foil substrates provide a more robust material for handling and coupling electrodes over energy storage devices using etched electrodes. The flexible foil substrates provide give under pressure and may be bent as they are assembled and coupled, whereas etched materials often break under light bending pressure.

Figure 1:
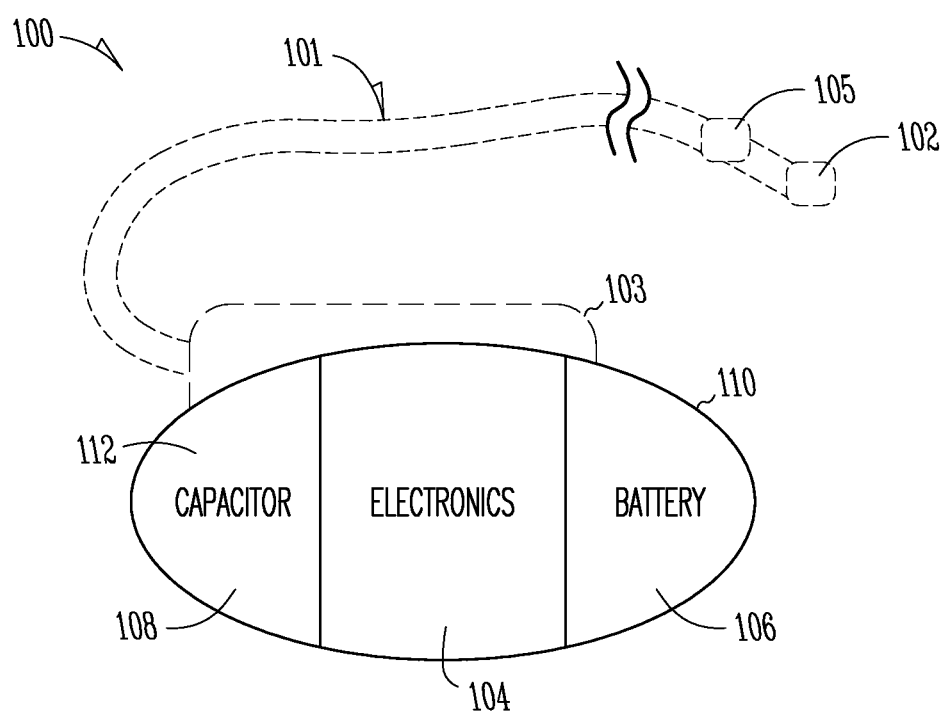
FIG. 1 is a schematic of a medical system including a sintered capacitor, according to some embodiments.

FIG. 1 is a schematic of a medical system 100 including a flexible foil capacitor, according to some embodiments. The medical system 100 represents any number of systems to provide therapeutic stimulus, such as to a heart. Examples of medical systems include, but are not limited to, implantable pacemakers, implantable defibrillators, implantable nerve stimulation devices and devices that provide stimulation from outside the body, including, but not limited to, external defibrillators.

Electronics 104 are to monitor the patient, such as by monitoring a sensor 105, and to monitor and control activity within the system 100. In some examples, the electronics 104 are to monitor a patient, diagnose a condition to be treated such as an arrhythmia, and control delivery of a stimulation pulse of energy to the patient. The electronics 104 can be powered wirelessly using an inductor. Alternatively, the electronics 104 can be powered by a battery 106. In some examples, electronics 104 are to direct small therapeutic bursts of energy to a patient from the battery 106.

For therapies, such as defibrillation, that use energy discharge rates exceeding what battery 106 is able to provide, a capacitor 108 is used. Energy from the battery 106 is controlled by the electronics 104 to charge the capacitor 108. The capacitor 108 is controlled by the electronics 104 to discharge to a patient to treat the patient. In some examples, the capacitor 108 completely discharges to a patient, and in additional examples, the capacitor is switched on to provide therapeutic energy and switched off to truncate therapy delivery.

Some examples of a medical system 100 include an optional lead system 101. In certain instances, after implantation, the lead system 101 or a portion of the lead system 101 is in electrical communication with tissue to be stimulated. For example, some configurations of lead system 101 contact tissue with a stimulation electrode 102. The lead system 101 couples to other portions of the system 100 via a connection in a header 103. Examples of the system 101 use different numbers of stimulation electrodes and/or sensors in accordance with the needs of the therapy to be performed.

Additional examples function without a lead 101. Leadless examples can be positioned in contact with the tissue to be stimulated, or can be positioned proximal to tissue to shock the tissue to be stimulated through intermediary tissue. Leadless examples can be easier to implant and can be less expensive as they do not require the additional lead components. The housing 110 can be used as an electrode in leadless configurations.

In certain embodiments, the electronics 104 include an electronic cardiac rhythm management circuit coupled to the battery 106 and the capacitor 108 to discharge the capacitor 108 to provide a therapeutic defibrillation pulse. In some examples, the system 100 includes an anode and a cathode sized to deliver a defibrillation pulse of at least approximately 50 joules. Other configurations can deliver larger amounts of energy. Some configurations deliver less energy. In some examples, the energy level is predetermined to achieve a delivered energy level mandated by a governing body or standard associated with a geographic region, such as a European country. In an additional embodiment, the anode and cathode are sized to deliver a defibrillation pulse of at least approximately 60 joules. In some examples, this is the energy level is predetermined to achieve an energy level mandated by a governing body of another region, such as the United States. In some examples, electronics 104 are to control discharge of a defibrillation pulse so that the medical system 100 delivers only the energy mandated by the region in which the system 100 is used. In some examples, a pulse of 36 joules is delivered.

Packaging anodes and cathodes can reduce their efficiency. Interconnections between conductors coupled to electronics and to the electrodes of the capacitor 108 decrease efficiency, for example. Accordingly, anodes and cathodes are sized to compensate for decreases in efficiency. As such, in some embodiments, the capacitor 108 includes anodes and cathodes sized and packaged to deliver a defibrillation pulse of at least approximately 50 joules. Some are sized and packaged to deliver a defibrillation pulse of at least approximately 60 joules.

One characteristic of some sintered electrode examples is that at least one anode and a cathode have a DC capacitance that is approximately 23% greater than a AC capacitance for the at least one anode and the cathode of an etched capacitor that has 74.5 microfarads per cubic centimeter. In some examples, the at least one anode and the cathode have an AC capacitance of at least 96.7 microfarads per cubic centimeter at 445 total voltage. In some examples, this is comparable to an operating voltage of about 415 volts. This is a 30% improvement over an etched capacitor that has 74.5 microfarads per cubic centimeter. Total voltage is the voltage that allows 1 milliamp of leakage per square centimeter. Some examples are aged to 415 volts.

In certain examples, the capacitor 108 includes a capacitor case 112 sealed to retain electrolyte. In some examples, the capacitor case 112 is welded. In some instances, the capacitor case 112 is hermetically sealed. In additional examples, the capacitor case 112 is sealed to retain electrolyte, but is sealed with a seal to allow flow of other matter, such as gaseous diatomic hydrogen or a helium molecule. Some of these examples use an epoxy seal.

A hermetically sealed device housing 110 is used to house components, such as the battery 106, the electronics 104, and the capacitor 108. Hermeticity is provided by welding components into the hermetically sealed device housing 110, in some examples. Other examples bond portions of the housing 110 together with an adhesive such as a resin based adhesive such as epoxy. Accordingly, some examples of the housing 110 include an epoxy sealed seam or port. Several materials can be used to form housing 110, including, but not limited to, titanium, stainless steel, nickel, a polymeric material, or combinations of these materials. In various examples, the housing 110 and the case 112 are biocompatible.

The capacitor 108 is improved by the present electrode technology in part because it can be made smaller and with less expense. The improvement provided by these electrodes is pertinent to applications where high-energy, high-voltage, or space-efficient capacitors are desirable, including, but not limited to, capacitors used for photographic flash equipment. The present subject matter extends to energy storage devices that benefit from high surface area sintered electrodes including, but not limited to, aluminum. The electrodes described here can be incorporated into cylindrical capacitors that are wound, in addition to stacked capacitors.

Figure 2:
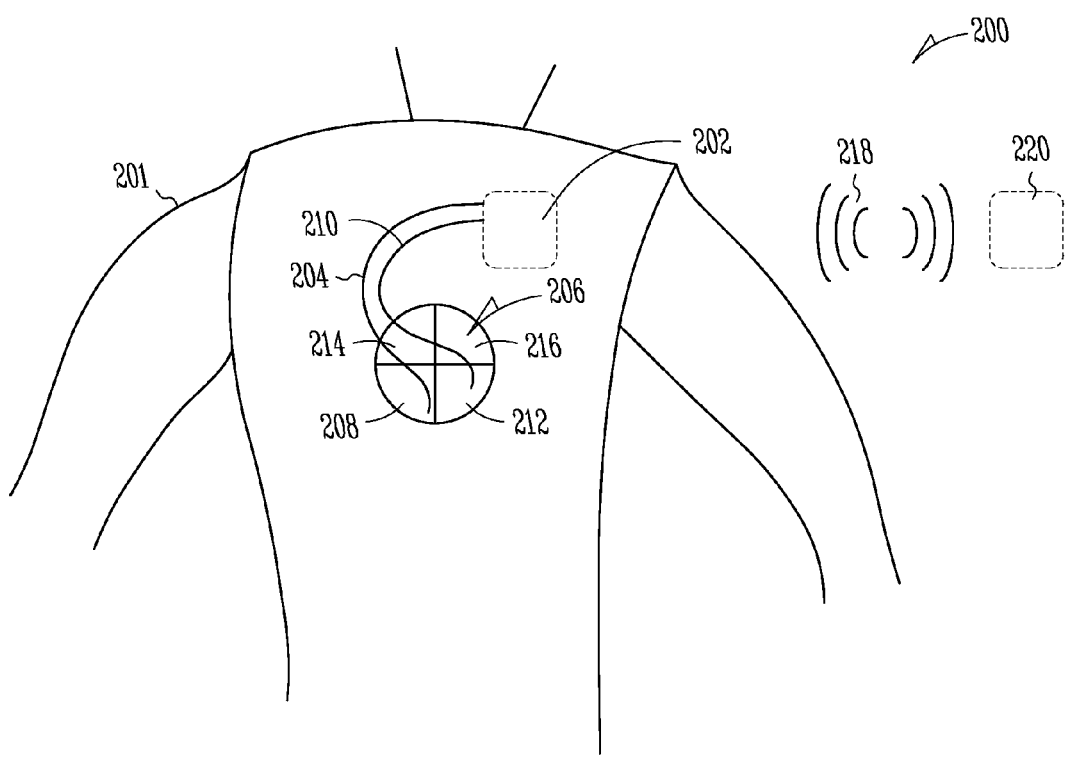
FIG. 2 is an implanted medical system including a sintered capacitor, according to some embodiments.

FIG. 2 is an implanted medical system 200, implanted in a patient 201, and including a sintered capacitor, according to some embodiments. The system includes a cardiac rhythm management device 202 coupled to a first lead 204 to extend through the heart 206 to the right ventricle 208 to stimulate at least the right ventricle 208. The system also includes a second lead 210 to extend through the heart 206 to the left ventricle 212. In various embodiments, one or both of the first lead 204 and the second lead 210 include electrodes to sense intrinsic heart signals and to stimulate the heart. The first lead 204 is in direct contact (e.g., touching) with the right atrium 214 and the right ventricle 208 to sense and/or stimulate both those tissue regions. The second lead 210 is in direct contact with the left atrium 216 and the left ventricle 212 to sense and/or stimulate both those tissue regions. The cardiac rhythm management device 202 uses the lead electrodes to deliver energy to the heart, either between electrodes on the leads or between one or more lead electrodes and the cardiac rhythm management device 202. In some examples, the cardiac rhythm management device 202 is programmable and wirelessly communicates 218 programming information with a programmer 220. In some examples, the programmer 220 wirelessly 218 charges an energy storage device of the cardiac rhythm management device 202.

The capacitor includes an anode and a cathode separated by a dielectric. The capacitor may be coupled to electronics adapted to charge the capacitor and use the energy for various purposes such as delivering therapy via an implantable medical device. In various embodiments, the capacitor includes one or more sintered anode layers. In some embodiments, the anode layers are electrically coupled together to provide a desired energy density.

Figure 3:
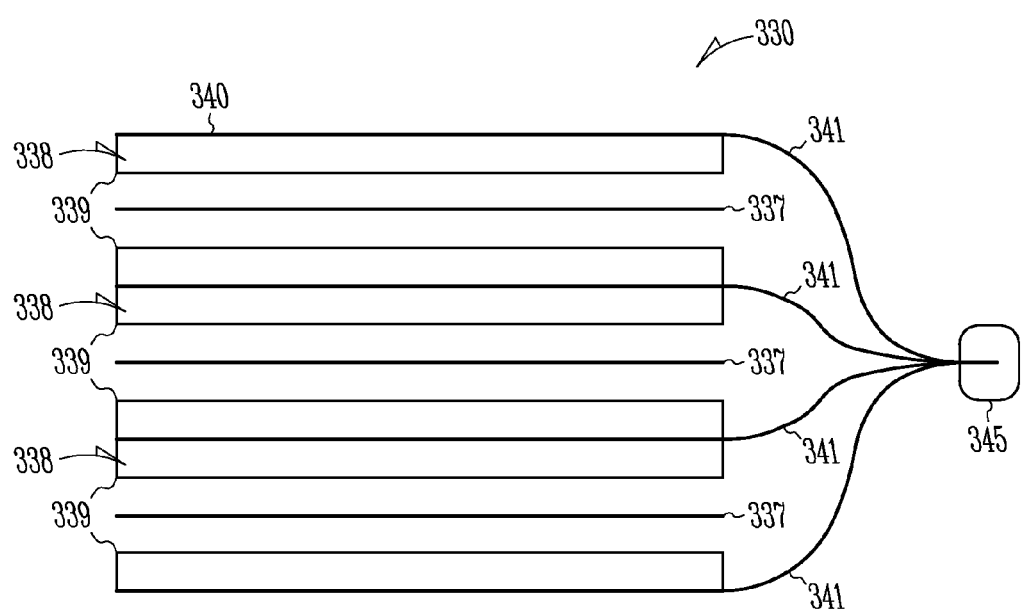
FIG. 3 shows a capacitor element according to an embodiment of the present subject matter.

FIG. 3 shows a capacitor element according to an embodiment of the present subject matter. The capacitor element 330 includes a number of electrodes, including a number of cathode stacks 337 and a number of anode layers 338. In various embodiments, the electrodes include foil, such as an aluminum foil. Cathode stacks 337 include a cathode including a cathode foil, such as a flexible foil in some embodiments. In various embodiments, the cathode stack 337 includes separator material disposed between the cathode foil and adjacent anode layers. The separator material may include electrolyte in some embodiments. In the illustrated embodiment, the anode layers include a sintered material. The sintered anode layers include a sintered material 339 disposed on a foil substrate 340. The foil provides a more robust electrode than, for example, an etched electrode, because the foil is more flexible and, thus more resistant to breaking when bent or folded. In various embodiments, the foil is more flexible than the sintered material. The flexible substrate may deform substantially more than an etched substrate to accommodate displacement between connected components during manufacturing as well as throughout the life of the capacitor element. Deformability of foil-based electrodes provide better manufacturing yields and reduces component failures over etched based electrodes. A tab 341 is coupled to each anode substrate 340 and the tabs 341 are connected together. In various embodiments, the tabs 341 may be continuous portions of the anode substrate 340. In some embodiments, the tab 341 may include a portion of the anode substrate and a separate conductive material coupled to the portion of the anode substrate. Some embodiments may include a separate conductive material coupled to the anode substrate to form the tab 341. In various embodiments, the cathode stacks include foil. In such embodiments, a clip may be used to couple the cathode stacks together, both mechanically and electrically. In the illustrated embodiment, the capacitive element is shown in an exploded view.

The tabs 341 are gathered and coupled together in a clip 345. A clip 345 is used to couple the tabs together. In various embodiments, the tabs 341 may be gathered and coupled together, such as by welding or soldering, prior to assembly into the clip 345. In some embodiments, the tabs 341 are secured with the clip 345 using one or more techniques such as crimping, welding or soldering. The clip 345 may be used to couple electrodes to other capacitor elements such as, a case, a feedthrough, other electronics, other electrode, other electrode groups, or combinations thereof. In various embodiments, the clip is to crimp tabs together. In some examples, the clip is elastically deformed to couple the tabs to one another. In additional embodiments, the clip is inelastically deformed to couple the tabs. In some examples, the clip is cold welded to one or more tabs. In some examples, the clip is aligned to one or more tabs. In various embodiments, an electrode may include multiple tabs. Such a configuration allows for various capacitor element connection schemes including, for example, to partition a capacitor stack into two or more capacitive elements.

Figure 4:
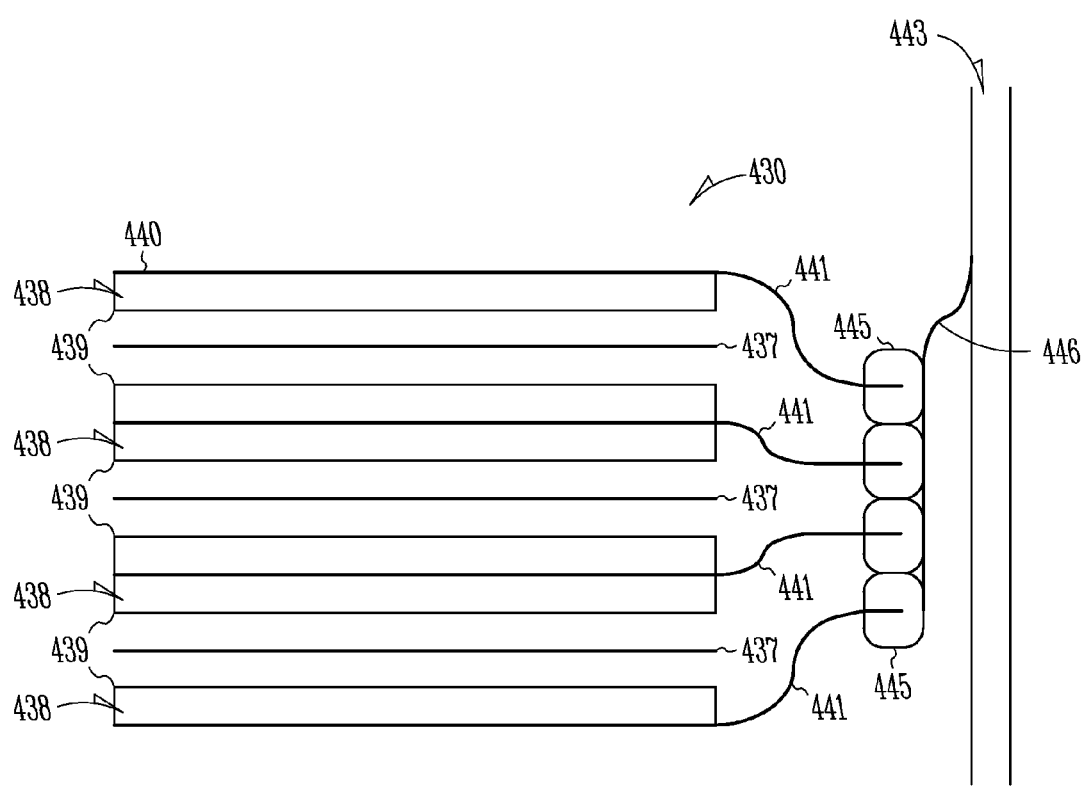
FIG. 4 shows a capacitive element according to an embodiment of the present subject matter.

FIG. 4 shows a capacitive element according to an embodiment of the present subject matter. The capacitive element 430 includes a number of electrodes including a number of cathode stacks 437 and a number of sintered anode layers 438. A cathode stack includes a cathode layer, the sintered anode layers include a sintered material 439 disposed on a substrate 440, such as a flexible foil substrate. In some examples, the sintered material 429 is sintered onto the substrate 440. A tab 441 is coupled to each anode substrate 440 and the tabs 441 are coupled together. The tabs 441 are coupled together using a clip 445 coupled to each tab 441. In some embodiments, the electrode does not include a tab and the clip couples to a sinter-free portion of the substrate. The clips 445 are coupled together using a weld for example. It understood that other methods of coupling the clips together are possible including, but not limited to, mechanical coupling, cold welding, laser welding, ultrasonic welding, or combinations thereof. Such coupling methods may be used to couple the tabs 441 to the clips 445, as well as, crimping the tabs in the clips.

In various embodiments, clips are coupled to other components, for example, other capacitive elements. In some examples, a plurality of clips are coupled together, then coupled to a second component. In additional embodiments, at least one clip is individually coupled to another component. In some of these embodiments, a plurality of layers are placed into electrical communication via the other component. Other components include, but are not limited to, tabs, feedthroughs, terminals, and other conductive materials. In the illustrated embodiment, the clips 445 are coupled to a case 443 enclosing the capacitive element 430. A ribbon of conductive material 446, or a wire, may be used to couple the clips 445 to the case 443. In various embodiments, the clips may be directly coupled to the case.

Figure 5:
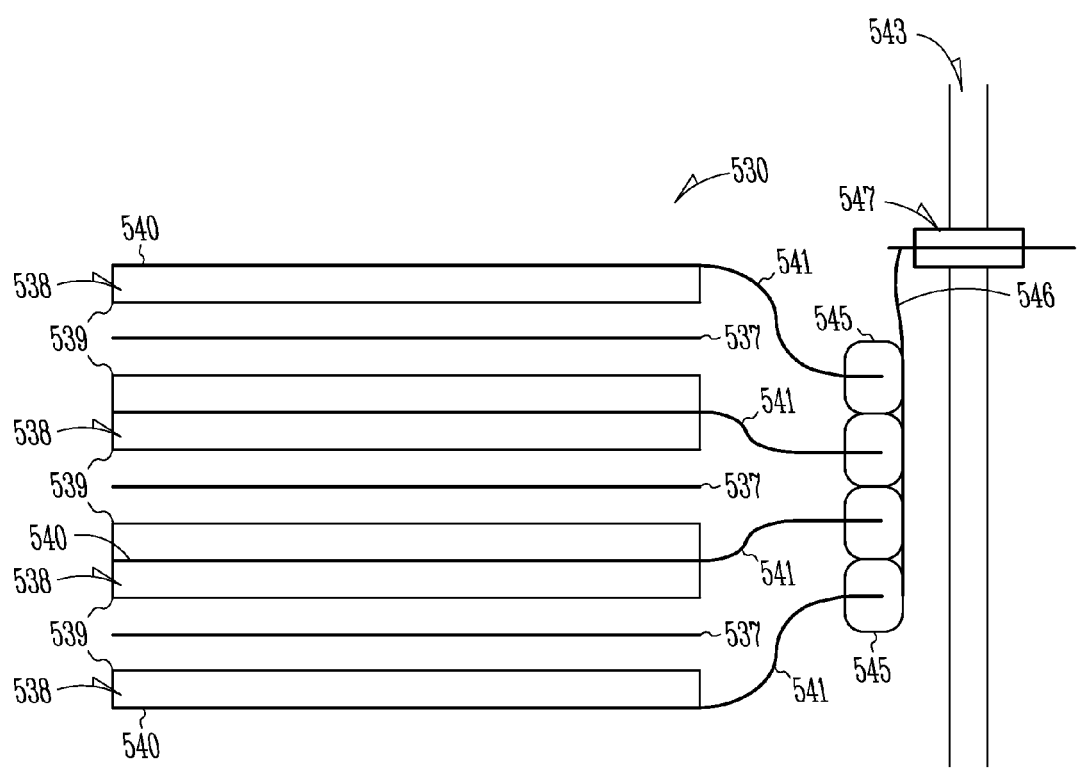
FIG. 5 shows a capacitive element according to an embodiment of the present subject matter.

FIG. 5 shows a capacitive element according to an embodiment of the present subject matter. The capacitive element 530 includes a number of cathode stacks 537 and a number of sintered anode layers 538. The sintered anode layers include a sintered material 539 disposed on a substrate 540. A tab 541 is coupled to each anode substrate 540 and the tabs 541 are connected together. The tabs 541 are coupled together using a clip 545 coupled to each tab 541. The clips 545 are coupled together using a weld for example. Other methods of coupling the clips together are possible, including, but not limited to, mechanical coupling, such as by a pin, cold welding, laser welding, ultrasonic welding, or combinations thereof. Such coupling methods may be used to couple the tabs to the clips. Crimping the tabs in the clips is also another method that may be used in some embodiments.

In various embodiments, the set of coupled clips are coupled to other components, for example, other capacitive elements. In the illustrated embodiment, the clips 545 are coupled to a feedthrough 547 of a case 543 enclosing the capacitive element 530. A ribbon of conductive material 546, or a wire, may be used to couple the set of clips 545 to the feedthrough 547. In some embodiments, the clips are coupled to a case enclosing the capacitive elements. In various embodiments, the clips may be directly coupled to the case.

FIG. 5 shows the stack of anode layers 538 and cathode stacks 537 in an exploded view. In various embodiments, the clips 545 are sized such that the separation between each clip slot is substantially the same as the separation of adjacent anode layers in the assembled stack. Configuring the clips as such reduces stress on the electrode tabs. This can extend the life of the capacitor by reducing the number of instances of tab breakage.

Figure 6A:
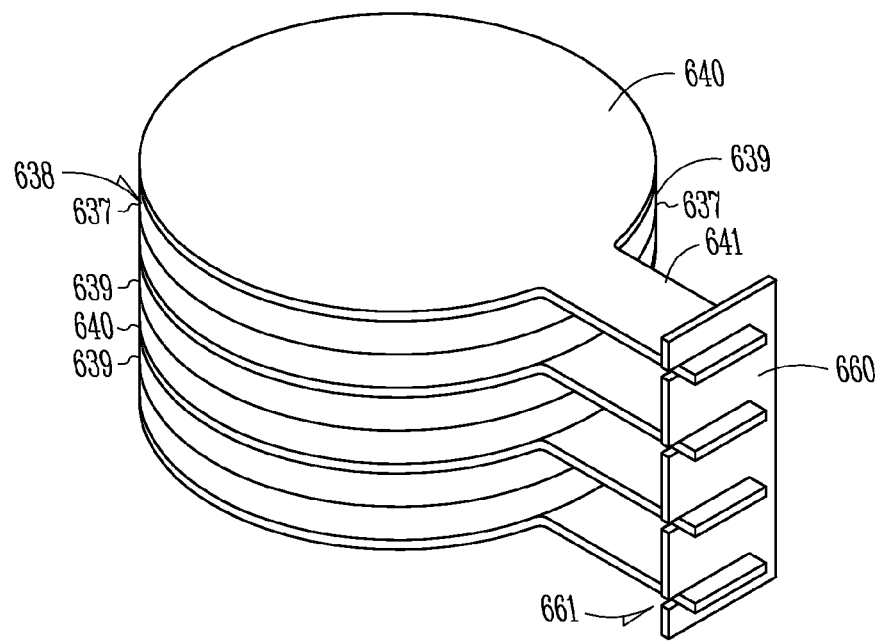
FIGS. 6A and 6B show a capacitive element according to embodiments of the present subject matter.
Figure 6B:
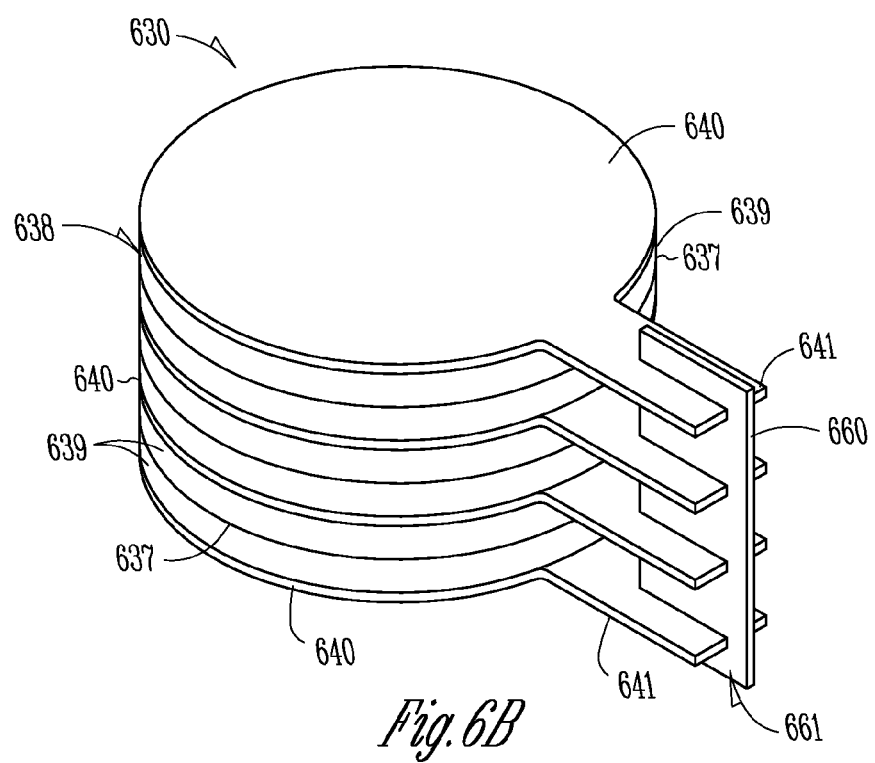

FIGS. 6A and 6B show a capacitive element according embodiments of the present subject matter. The capacitive element 630 of FIG. 6A shows a number of electrodes including a number of cathode stacks 637 and a number of anode layers 638 stacked to form the capacitive element 630. Cathode stacks 637 may include a cathode foil, such as a flexible foil in some embodiments. In various embodiments, the cathode stack 637 includes separator material disposed between the cathode foil and adjacent anode layers. The separator material may include electrolyte in some embodiments.

The anode layers 638 include a sintered material 639 deposited on a substrate 640, such as a flexible foil substrate. In various embodiments, the sintered material 639 and the substrate 640 include aluminum. The anode layers 638 include a tab 641 extending from the layer. In various embodiments, the tab 641 is a continuous, monolithic and solid portion of the anode substrate 640. In some embodiments, the tab includes a separate piece of material coupled to the anode layer.

Also shown in the embodiment of FIG. 6A is an interconnect 660 to couple the tabs 641 of the anode layers together. The interconnect 660 includes a series of slots 661, with the interconnect defining a comb shape. In some examples, the slots 661 are spaced apart to substantially match the separation of the tabs 641 extending from the anode layers. After a tab is positioned in a slot of the connector, the tab is coupled to the connector. Methods of coupling the tab to the connector include, but are not limited to, welding, soldering, crimping, or combinations thereof.

FIG. 6B shows a slotted, comb-type interconnect 660 coupled to the tabs 641 of a capacitor element 630 where the interconnect 660 is oriented 90 degrees from that shown in FIG. 6A. Other orientations of the interconnect are possible without departing from the scope of the present subject matter. Various orientations may be better adapted to the shape of a particular capacitor element or the space available within a case enclosing the capacitor element, or combinations thereof.

FIG. 7 shows a capacitor element according to an embodiment of the present subject matter. The capacitor element 730 includes a number of cathode stacks 737 and a number of sintered anode layers 738 stacked together. The anode layers 738 include a sintered material 739 deposited on a substrate 740, such as a foil. Anode tabs 741 extend from the substrate 740. The anode tabs 741 are coupled together using a slotted interconnect 760. The slots 761 of the slotted interconnect 760 are spaced to substantially match the separation of the anode layers 738, thus minimizing stress on the tabs and, in some instances, reducing the chance of damaging the anode tab or substrate. In various embodiments, the slotted interconnect is coupled to a case enclosing the capacitor element. The anodes of the illustrated capacitive element are coupled to a case 743 using a ribbon of conductive material 746. Methods of coupling the ribbon of conductive material to the case include, but are not limited to, welding soldering, mechanical coupling such as by crimping, or combinations thereof.

Figure 8:
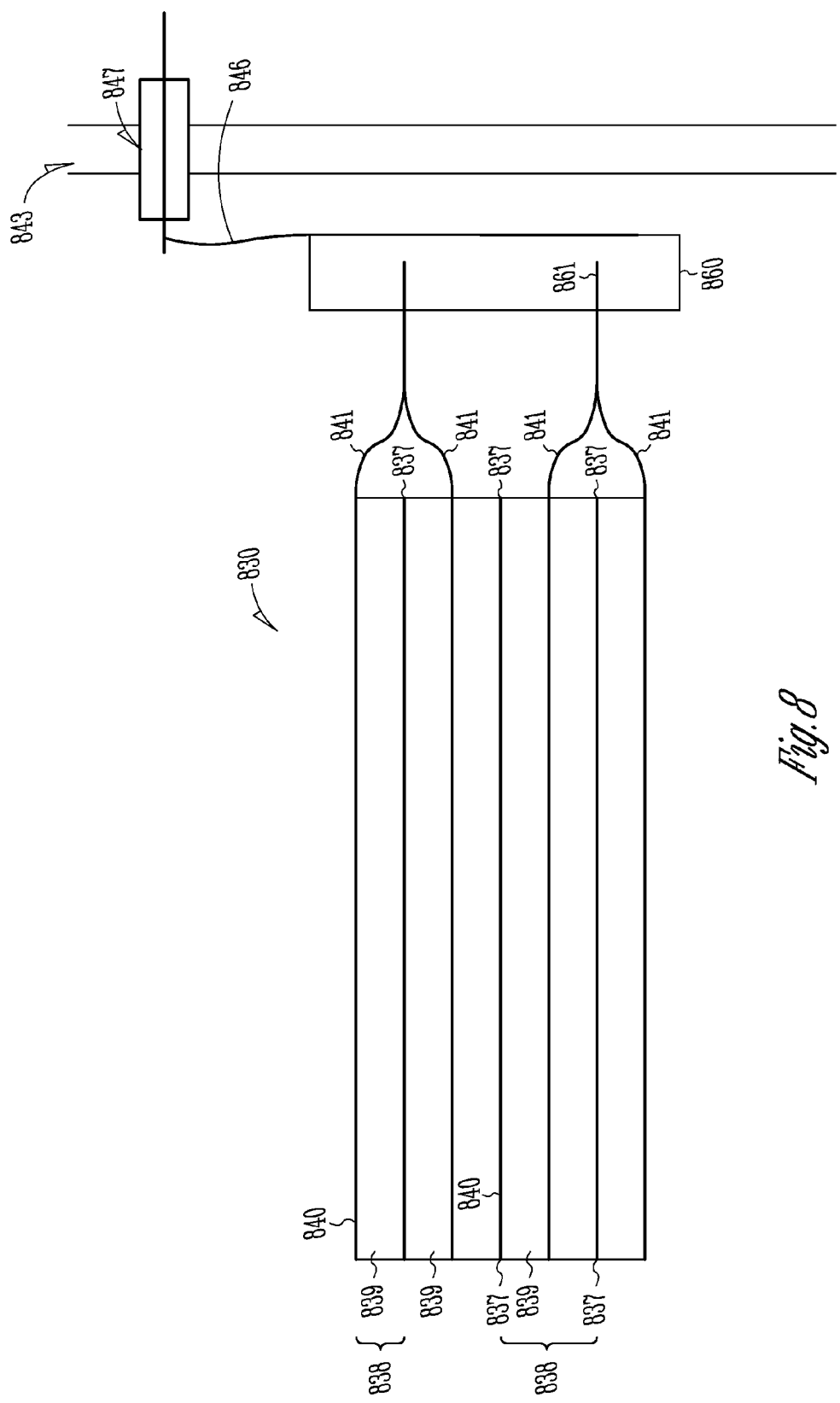
FIG. 8 shows a capacitive element according to an embodiment of the present subject matter.

FIG. 8 shows a capacitive element according to an embodiment of the present subject matter. The capacitive element 830 includes a number of electrodes including an assembly of cathode stacks 837 and an assembly of anode layers 838 stacked to form the capacitive element 830. Each cathode stack 837 includes a cathode foil. In various embodiments, a cathode stack 837 includes separation material disposed between the cathode foil and adjacent anodes. In some embodiments, the separation material includes electrolyte. The anode layers 838 include a sintered material 839 disposed on a substrate 840.

Anode tabs 841 extend from each anode layer. The anode tabs 841 are coupled together using a slotted comb-type interconnect 860. Multiple anode tabs 841 may be coupled in a slot 861 of the slotted interconnect 860. The illustrated embodiment, shows pairs of tabs 841 gathered and coupled in each slot 861 of the slotted interconnect 860. In certain examples, each slot of the slotted interconnect may have other numbers of anode tabs coupled together. The slotted interconnect 860 is coupled to a feedthrough 847 of a case 843 enclosing the capacitive element 830.

In some embodiments, the interconnect 860 may be directly coupled to the feedthrough 847. In the illustrated embodiment, the slotted interconnect 860 is coupled to the feedthrough 847 using a ribbon of conductive material 846. Such a configuration may allow the anodes to be insulated from the case, and may allow the anodes to be coupled with other electronics, such as electronics of an implantable medical device.

Figure 9A:
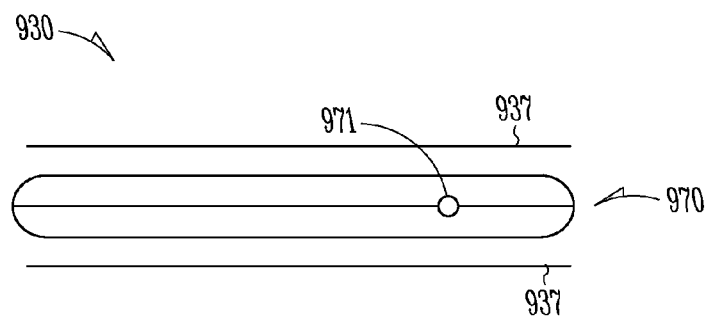
FIG. 9A shows an exploded view of a capacitive element according to an embodiment of the present subject matter.
Figure 9B:
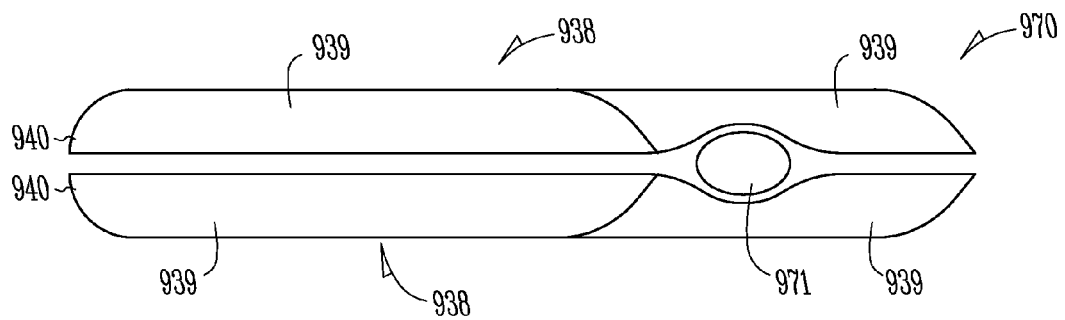
FIG. 9B shows a cross-section of anode components according to an embodiment of the present subject matter.

FIG. 9A shows an exploded view of a capacitive element according to an embodiment of the present subject matter. The capacitive element 930 includes a number of cathode stacks 937 and a number of anode components 970 stacked to form the capacitive element 930. The cathode stacks 937 include a cathode foil. In various embodiments, the cathode stacks include a separator material disposed between the cathode foil and adjacent anode components. In some embodiments, the separator material includes electrolyte. The anode components 970 include two anode layers 938 with a wire 971 snaked between them. Each anode layer includes sintered material 939 disposed on a substrate 940, such as a foil. FIG. 9B shows a cross-section of the anode components 970. Each anode includes a pattern of sintered material 939 on one side of the substrate 940.

The anode layers 938 are stacked such that the sinter-free sides if each anode substrate 940 is proximate the other. A wire 971, or ribbon of conductive material, is disposed between the anode layers 938. In some examples, the wire 971 is disposed at least partially into the stack, with a substrate connection portion 941 (FIG. 9C) bunched around the wire 971. In some examples, a connection portion of a second electrode is bunched around the conductive interconnect. In some examples, the substrate connection portion 941 and the connection portion of the second electrode conformed to the conductive interconnect. The wire 971 assists lateral charge migration in the capacitive element thus reducing the equivalent series resistance (ESR) of the capacitive element.

Figure 9C:
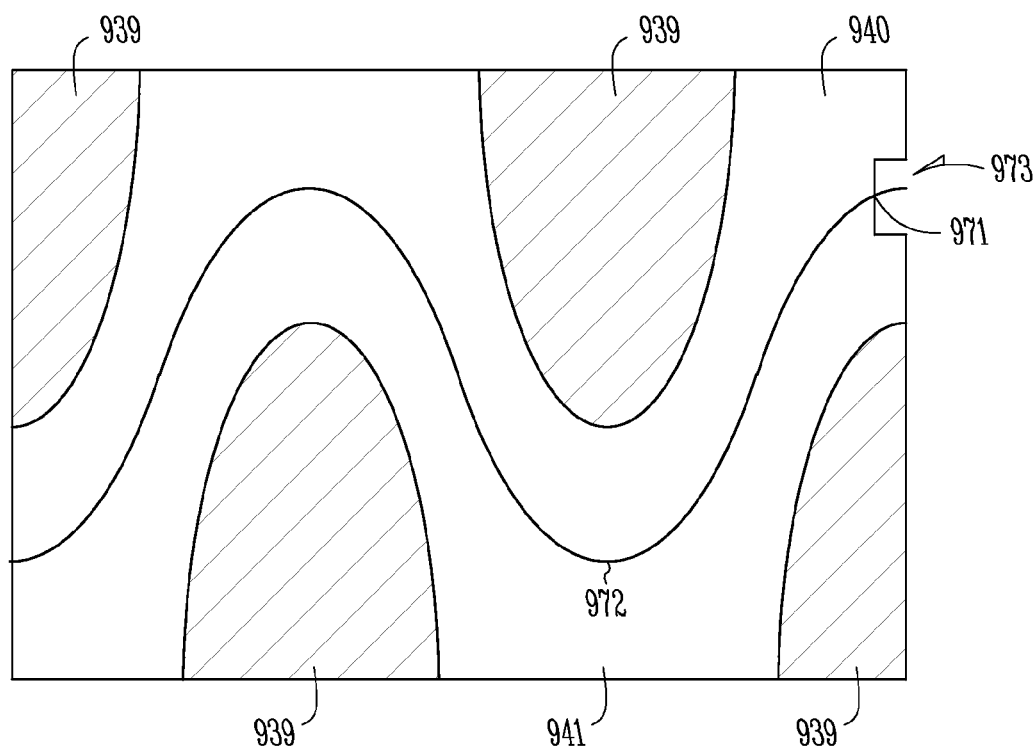
FIG. 9C shows a sintered pattern according to an embodiment of the present subject matter.

FIG. 9C shows a sintered pattern according to an embodiment of the present subject matter. FIG. 9C also shows the location of a wire path 972 between the anode layers 938. Note that the wire path proceeds through areas where the substrate is free of sintered material. This allows the wire 971 to be disposed in a recess formed between the anode layers 938 without creating a bulge that effects the stacking of additional capacitor element components. It is understood that other sintered patterns are possible without departing from the scope of the present subject matter.

In various embodiments, an anode layer 938 includes a recess 973 to provide access to the wire 971 or conductive ribbon of material. In some embodiments, the wire 971, or conductive ribbon of material, extends from the anode layers 938 for coupling with other components such as other anode layers. In such embodiments, the extending wire, or ribbon of conductive material, is akin to the anode tabs described above. As such, the anodes may be connected together using a weld, using a clip, using a slotted connector, or combination thereof. Additionally, the anodes may be coupled to a case, or a feedthrough extending through the case.

This application is intended to cover adaptations or variations of the present subject matter. It is to be understood that the above description is intended to be illustrative and not restrictive. The scope of the present subject matter should be determined with reference to the appended claims, along with the full scope of legal equivalents to which such claims are entitled.

What is claimed is:

1. An apparatus comprising:
an electrode;
a separator stacked in alignment with the electrode;
a first electrode assembly disposed in a stack with the electrode and the separator, the separator disposed between the electrode and the first electrode assembly to physically separate the electrode and the first electrode assembly,
wherein the first electrode assembly includes:
a first layer including a first conductive material deposited on a first substrate, the first substrate having a first substrate flexibility greater than a first material flexibility of the first material; and
a second layer stacked with the first layer, the second layer including a second conductive material deposited on a second substrate, the second substrate having a second substrate flexibility greater than a second material flexibility of the second material; and
an interconnect coupled to the first substrate and the second substrate to physically and electrically couple the first layer and the second layer of the stack,
wherein the first substrate of the first layer and the second substrate of the second layer are proximate each other and between the first material and the second material,
wherein the interconnect includes a conductive element disposed between the first substrate and the second substrate,
where at least one of the first layer and the second layer includes a notch configured to expose the conductive element disposed between the first substrate and the second substrate.

2. The apparatus of claim 1, wherein the first layer includes a first tab extending from a first location along a perimeter of the first layer.

3. The apparatus of claim 2, wherein the second layer includes a second tab extending from a second location, other than the first location, along the perimeter of the first layer.

4. The apparatus of claim 2, wherein the second layer includes a second tab extending from the first location along a perimeter of the second layer, and wherein the first tab is coupled to the second tab using the interconnect.

5. The apparatus of claim 4, including a weld to couple the first tab with the second tab.

6. The apparatus of claim 4, wherein the interconnect includes a clip.

7. The apparatus of claim 4, wherein the interconnect includes a comb interconnect.

8. The apparatus of claim 7, wherein the first tab and the second tab are coupled together in a single slot of the comb interconnect.

9. The apparatus of claim 7, wherein the first tab and second tab are coupled together using separate slots of the comb interconnect.

10. The apparatus of claim 1, wherein the first material and the second material includes sintered material, and
wherein the first substrate and the second substrate include sintered material on only one major surface of each respective substrate.

11. The apparatus of claim 1, wherein the first substrate and the second substrate are substantially sinter-free along a path of the conductive element.

* * * * *